United States Patent [19]

Walters et al.

[11] Patent Number: 4,992,151

[45] Date of Patent: Feb. 12, 1991

[54] METHOD FOR THE SELECTIVE ALPHA HALOGENATION OF ALKYLAROMATIC COMPOUNDS

[75] Inventors: Marlin E. Walters, West Columbia; George M. St. George; W. Frank Richey, both of Lake Jackson, all of Tex.

[73] Assignee: The Dow Chemical Company, Midland, Mich.

[21] Appl. No.: 472,507

[22] Filed: Jan. 29, 1990

[51] Int. Cl.$^5$ .................... C08G 63/00; C07C 22/00
[52] U.S. Cl. .................... 204/157.99; 528/176; 570/185; 568/726; 568/722
[58] Field of Search ............ 528/176; 204/157.99; 570/185

[56] References Cited

U.S. PATENT DOCUMENTS

| | | | |
|---|---|---|---|
| 2,813,132 | 11/1957 | Kundiger et al. | 204/157.99 |
| 3,251,887 | 5/1966 | Huyser | 568/656 |
| 3,424,803 | 1/1969 | Roberts et al. | 204/157.99 |
| 3,696,158 | 10/1972 | Relles | 570/193 |

FOREIGN PATENT DOCUMENTS

| | | | |
|---|---|---|---|
| 0632679 | 11/1978 | U.S.S.R. | |
| 0356107 | 8/1931 | United Kingdom | 204/157.99 |
| 1563164 | 7/1980 | United Kingdom | |

OTHER PUBLICATIONS

J. Am. Chem. Soc. 61, 2142 (1939).
Chem. Abst. 41:3437a (1947).
Nature 156, 369 (1945).
Organic Reactions, vol. 5, John Wiley & Sons, Inc. New York (1949), Ch. 1: "Synthesis of Acetylenes", pp. 21–22.
J. Org. Chem. 28, 3173 (1963).
J. Am. Chem. Soc. 82, 6108 (1965).
Macromol. 6,815, (1973).
J. Org. Chem. 39, 3472 (1974).
J. Org. Chem. 44, 2270 (1979).
J. Am. Chem. Soc. 105, 7672 (1983).
Polymer Preprints, 1986, Am. Chem. Soc., p. 889.
General Organic Chem. vol. 86, 1977 (29054g), "Dialkylaminosulfur Trifluorides as Fluorinating Agents", Middleton, William J.
Chemical Abstracts, vol. 90, 1979 (86971k), "Arylacetylenes", Gavrilov, L. D., et al.
General Organic Chem., vol. 107, 1987 (22708s), "Fluorination of Organic Carbonyl Compounds", Desbois, Michel.

Primary Examiner—Harold D. Anderson
Assistant Examiner—T. Mosley

[57] ABSTRACT

Inorganic and organic hypohalites are used to obtain good selectivity to alpha halogenation of alkyl aromatic compounds. Alkali and alkaline earth hypohalites must be used in conjunction with a phase transfer medium. Useful organic hypohalites are the tertiary alkyl hypohalites, which are employed in the presence of free radical generating media such as light or compounds which produce free radicals thermally. At least one mole of hypohalite reactant must be used for every alpha hydrogen in the alkyl aromatic compound.

A new bisphenol which contains biphenyl functionality has been made as well as an aromatic polyester derived therefrom.

30 Claims, No Drawings

METHOD FOR THE SELECTIVE ALPHA HALOGENATION OF ALKYLAROMATIC COMPOUNDS

BACKGROUND OF THE INVENTION

During the past fifty years the side chain chlorination of ethylbenzene has been studied with a number of different chlorinating agents including hypochlorites. Very good selectivity to alpha chlorination was observed, but only to monochlorination. There are no examples of a preparative method for the selective halogenation of alkylaromatics to compounds having at least two alpha halogen substituents, especially when beta hydrogens are present on the side chain.

Various references over the years have disclosed the chlorination of ethylbenzene using different chlorinating agents. The predominant product is α-chlorethylbenzene with some β-chlorethylbenzene or α,β-dichlorethylbenzene, but little or no α,α-dichloroethylbenzene. Representative references are J.Am.Chem. Soc. 61, 2142 (1939); Chem.Abst. 41:3437a (1947); Bull. soc.chim.Belges 59, 193(1950); J.Org.Chem. 28, 3173 (1963); J.Org.Chem. 39, 3472(1974) and J.Org.Chem. 44,2270(1979).

The chlorination of diethylbenzene in the presence of PCl$_5$ and light showed poor selectivity to multichlorination in the alpha positions [Macromol. 6, 815(1973)]. Analysis of the product of the reaction of meta-diethylbenzene with chlorine and PCl$_5$ conducted at 90°–100° C. with a 300w incandescent light lamp showed a reaction mixture containing "at least 25 different components of which 6–8 could be considered major constituents".

British patent No. 1,563,164 (1980) describes the preparation of α,α-dichloroethylaromatic compounds by a chlorination with molecular chlorine of the corresponding monochlorinated ethylaromatic compounds using a phosphorus halide catalyst, e.g. PCl$_3$ or PCl$_5$, in the presence of light or other initiator. Selectivities of 80–90% to the desired α,α-dichloroethylaromatic compounds are taught, but conversion of the ethylaromatic is only up to about 50%. A comparative example in which the same system was used starting with ethylbenzene gave a product mixture of 58.5% α-chloroethylbenzene, 31.5% α, α-dichloroethylbenzene, 6.8% α,β-dichloroethylbenzene and 3.2% higher chlorinated products.

In 1945 Prof. J. Kenner reported [Nature 156, 369(1945)] that his colleague Dr. R. F. Garwood had demonstrated that t-butyl hypochlorite in the presence of benzoylperoxide effectively chlorinated ethylbenzene to α-chloroethylbenzene. No experimental conditions, yields or the formation of any dichloro- products were mentioned.

In 1960 Walling initiated a series of studies on t-butyl hypochlorite as a chlorinating agent [J.A.C.S. 82, 6108(1960)]. These focused on kinetics and mechanism, and the reaction conditions involved large excesses of hydrocarbon over tert-butyl hypochlor-ite. In the case of the chlorination of alkylaromatics, little or no dichlorination was observed, and there is no mention of the selectivity to dichlorination.

U.S. Pat. No. 3,251,887 (1966) employs trichloromethanesulfonyl chloride in the presence of a free-radical generating catalyst to chlorinate ethylbenzene selectively to obtain (1-chlorethyl)benzene and states that in the case of ethylbenzene, tert-butyl hypochlorite gives no better selectivity to the alpha over the beta isomer in monochlorination than does the photochlorination with molecular chlorine.

Sodium hypochlorite (bleach) at a pH of 7.5–9 in the presence of phase transfer catalysts selectively chlorinates alkylaromatics in the alpha position [J.A.C.S. 105, 7672, (1983)]. For a 94% toluene conversion the product yields were: benzyl chloride (64%), benzal chloride (11%), with compounds such as benzoic acid, cresols, benzaldehyde, benzyl alcohol and ring chlorinated compounds making up the remainder. No attempt was made to optimize dichlorination and for the ethylbenzene reaction no product distribution was given.

SUMMARY OF THE INVENTION

Hypohalites are reacted with alkylaromatics having at least two alpha-hydrogens and at least one beta-hydrogen on each alkyl moiety to obtain halogenated alkylaromatic compounds containing at least two alpha-halogens with little or no beta-halogenated co-products.

Both inorganic and organic hypohalites can be used to obtain good selectivity to di-alpha halogenation. Alkali and alkaline earth hypohalites must be used in a phase transfer medium. Effective organic hypohalites are the tertiary alkyl hypohalites in the presence of a free radical generating medium, e.g. light, free radical generating catalysts or compounds which will thermally produce free radicals. At least one mole of hypohalite reactant must be used for every alpha hydrogen in the alkyl aromatic compound.

DETAILED DESCRIPTION OF THE INVENTION

The alkylaromatic compounds useful in the process of the invention are those which contain at least two alpha hydrogens, i.e., hydrogen atoms bonded to carbon atoms which are in turn bonded directly to an aromatic ring, and at least one beta hydrogen on each alkyl moiety, i.e. a hydrogen bonded to a carbon atom attached to an alpha-carbon on the aliphatic side-chain. Representative mono-substituted alkylaromatic compounds, wherein the alkyl side chain may contain 2 to 12 carbon atoms, are alkylbenzenes, alkylnaphthalenes, alkylanthracenes, alkylbiphenyls and the like compounds which possess at least two alpha hydrogens and at least one beta-hydrogen on each aliphatic side chain. Representative of this type of compound are ethylbenzene, n-propylbenzene, n-butylbenzene, n-octylbenzene, n-decylbenzene, n-dodecylbenzene ethylphenyl acetate, ethylnaphthalene, diethylbenzene, diethylnaphthalene, ethylanthracene, ethylbiphenyl, diethylbiepenyl, n-propylbiephenyl, ethylthiophene, phenethyl alcohol, indane, 1-indanone, indene, dihydro-coumarin, 2-ethylanthraquinone, 4-ethylacetophenone, 4-ethylphenol and the like. Also representative are di-, tri- and more highly substituted alkyl aromatics containing one alpha hydrogen and at least one beta-hydrogen per alkyl group such as diisopropyl benzene, diisopropyl biphenyl, diisopropyl naphthalene, triiso-propylbenzene and the like.

Other compounds which are precursors of the dialphahaloalkylaromatic compounds made by the process of the present invention are alkyl-substituted furans, thiophenes, pyridines, pyrazines, pyrroles and the like.

In one aspect of the invention an aromatic compound, having at least two alpha-hydrogens, and at least one beta-hydrogen on each alkyl moiety, is contacted with a halogenating agent which will preferentially substitute each alpha-hydrogen.

While chlorinating agents such as chlorine, phosphorous pentachloride and sulfuryl chloride are capable of chlorinating the α-carbon of the alkyl substituent, attempts at polychlorination cause numerous other chlorinated derivatives to be formed. Hypochlorites, when used as the means for the chlorination, are more selective and will cause the chlorines to substitute the α-hydrogens preferentially. Thus, for example, in the chlorination of ethylbenzene with t-butyl hypochlorite according to the present invention, the ratio of α,α-dichlorethylbenzene to other multichlorinated species is 90-100/1. This is illustrated in Examples 1, 3, 4, 5 and 6.

While an alkali metal hypohalite can be used in conjunction with a phase transfer catalyst, the preferred halogenating agent is a t-alkyl hypohalite such as t-butyl hypochlorite. In either method the amount of hypohalite must be at least two moles for each mole of the alkylaromatic compound. In the preferred method the alkyl-substituted aromatic compound and t-alkyl hypohalite are contacted in the presence of a free-radical generating medium, optionally in a solvent. The preferred tertiary alkyl hypohalites are t-butyl hypochlorite or t-amyl hypochlorite. the former being most preferred. For other t-alkyl hypochlorites see the table in Greene et al. J. Org. Chem. 28 55, (1963). The temperature of the reaction should be controlled so as prevent the thermal decomposition of the hypohalite. The byproduct alcohol is subsequently removed by distillation along with any solvent present, leaving the desired dialphahaloalkylaromatic compound.

The following equation, showing the dialphachlorination of ethylbenzene, is representative of the invention:

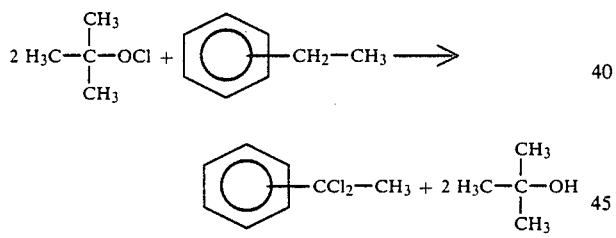

The temperature employed in the reaction is controlled at from about −70° C. to about 80° C., preferably at about 0° to 25° C. The t-alkylhypohalites will decompose at elevated temperatures, e.g. t-butyl hypochlorite will decompose explosively at temperatures in excess of 80° C.

The temperature is conveniently controlled by controlling the amount of light incident on the reaction mixture and by external cooling of the reactor. If the light source is removed the reaction ceases immediately. The reaction can also be stopped by the addition of air or oxygen to the reaction medium. The time of reaction is dependent upon the temperature and the light flux, but is generally complete within 2-3 hours.

Free radical catalysts useful in the invention are, for example, peroxides such as t-butyl peroxide and t-amyl peroxide and hydroperoxides such as chloro-t-butyl hydroperoxide, cumene hydroperoxide and cyclohexane hydroperoxide.

Compounds which produce free-radicals thermally which are useful in the invention are diazo compounds such as azobisisobutyronitrile and diacyl peroxides such as isobutyroyl peroxide.

Solvents useful for the reaction are aromatic hydrocarbons having from 6 to 12 carbon atoms. The halogenated derivatives of aliphatic and aromatic hydrocarbons, especially the chlorinated derivatives, are also useful. The hypohalites themselves can serve as solvents for the reaction.

The ratio of reactants employed is at least two moles of the alkali metal or t-alkyl hypohalite for each mole of the alkylaromatic hydrocarbon. Operable limits are from about 2 to about 2000 moles of the hypohalite per mole of alkylaromatic compound; the preferred range of hypohalite being from about 2 to about 10 moles per mole of alkylaromatic compound.

The di-, tri-, tetra- and higher alphahaloalkyl products of the halogenation reaction are useful in the preparation of the corresponding di-, tri- tetra- and higher phenols by reacting these halogenation products with a phenol. These polyphenols are valuable precursors to high performance engineering thermoplastics such as polycarbonates and polyarylates, or in high performance cross-linked polymers such as epoxy resins. Alternatively the alphahaloalkyl products of the invention can be dehydrohalogenated to form alkynylaromatic compounds. The di- and triethynyl aromatic compounds are valuable precursors to thermosetting polyphenylenes. Some such products are available commercially as "H-Resins" from Hercules Inc.

The following examples are representative of the invention:

EXAMPLE 1.

Preparation of 1,1-dichloroethylbenzene by phase transfer chlorination of ethylbenzene.

A solution of sodium hypochlorite (1000 mL of bleach, 5.25% NaOCl, 52.5g, 0.70 mole) is placed into a 2-liter, 5-neck flask equipped with thermometer, pH probe and a mechanical stirrer. The pH is adjusted from 12.5 to 8.0 with conc. HCl. Methylene chloride (250 mL, 331g, 2.22 moles) is added, followed by tetrabutylammonium bromide (6.45g, 0.02 mole) and t-butyl alcohol (0.76 mL, 0.6g, 0.008 mole). Ethylbenzene (12.23 mL, 10.6g, 0.10 mole) is added at once and the mixture is stirred vigorously. The pH of the solution drops to 7.10 as the temperature rises from an initial 25° C. to 38° C. in 30 minutes. Gas chromatography (GC) analysis at this point shows no ethylbenzene remaining. The product mixture contains 1,1-dichloroethylbenzene (78%), 1-chlorostyrene (7%), 1-chloroethylbenzene (3%), 2-chloroethylbenzene (2%) and acetophenone (10%).

EXAMPLE 2.

Preparation of 1,1,1′,1′-tetrachloroethylbenzene from diethylbenzene using an alkali metal hypochlorite and a phase transfer catalyst.

In the manner of Example 1, aqueous NaOCl (1000 mL, 55 g, 0.72 mole) is placed in an identical flask equipped in the same fashion. The pH of the solution is adjusted as before to 8.0 and 250 mL of $CH_2Cl_2$ is added, followed by 6.71 g (0.05 mole) of diethylbenzene and 6.45 g (0.02 mole) of tetra-n-butylammonium bromide. After 30 min. of stirring, the temperature of the mixture rises from 25° C. to 37.8° C., and the pH to 8.45. At this time G.C. analysis shows no remaining diethylbenzene and only a single product. The stirring is stopped and the phases are allowed to separate. The organic phase is dried with MgSO$_4$, filtered and the solvent is removed on a rotary evaporator to give a pale yellow residual oil (13.52 g, 99% theoretical) which is shown by NMR analysis to be the desired 1,1,1',1'-tetrachloroethylbenzene.

The following examples are conducted according to the most preferred method, i.e. employing t-butyl hypochlorite as the chlorinating agent.

EXAMPLE 3.

Preparation of 1,1-dichloroethylbenzene using t-butyl hypochlorite.

Into a 5-neck 2-liter flask, equipped with thermometer, mechanical stirrer and a pH probe, is placed 1000 mL of an aqueous bleach solution (~5.25% NaOCl). The flask is placed in an ice bath and cooled to 8° C. and t-butyl alcohol (56.5 mL, 0.59 mole) and glacial acetic acid (34.35 mL) are added with stirring. The temperature rises to about 15° C. and the pH drops from about 11.3 to about 6.5. Stirring is continued for about five minutes and then allowed to phase-separate, during which time a yellow oil floats to the surface. Ethylbenzene (36.9 mL, 0.30 mole) is added, stirring resumed and a 275-watt sun lamp is placed over the flask. The mixture is stirred with illumination for one hour while the temperature is maintained within the range of 8°-18° C., after which stirring is stopped and the mixture is allowed to phase-separate.

The aqueous phase is extracted with two × 100 mL portions of methylene chloride and combined with the organic phase. The combined solvent and organic phase is then dried over MgSO$_4$ and the solvent is removed by distillation, leaving 52.01 g of oil. G.C. analysis shows that the product is 73.6% 1,1-dichloroethylbenzene, 10.34% 1-chloroethylbenzene and 10.48% acetophenone and some minor impurities.

The following three experiments (Examples 4, 5 and 6) show the use of other solvents in the reaction using t-butyl hypochlorite as the chlorinating agent.

EXAMPLE 4.

Use of Carbon tetrachloride as Solvent.

A quantity of t-butyl hypochlorite (7.0 mols, 759.99 g, 775 mL) is chilled to −5° C. in a brine jacketed reaction flask equipped with mechanical stirrer, light well, thermometer and nitrogen supply. Ethylbenzene (2.0 mole, 213.4 g, 246 mL) in CCl$_4$ (10.4 moles, 1594 g, 1000 mL) is added to the reactor and the reaction is started by turning on the lamp (incandescent, 25 watt lamp, General Electric model FG648-X). The reaction temperature is allowed to rise to 10° C. and samples are taken periodically for G.C. analysis. After 4 hours the reaction is complete and the mixture is drained from the reactor and the t-butanol is stripped using a rotary evaporator which leaves 322.62 g of a colorless oil which is 89.4% 1,1-dichloroethylbenzene by G.C. analysis (82.3% yield).

EXAMPLE 5.

Use of Benzene as Solvent.

The reaction of Example 4 is repeated except that benzene (11.18 moles, 874 g, 1000 mL) is used in place of carbon tetrachloride. The t-butanol is removed on a rotary evaporator and there remains 341 g of a colorless oil which is 91.7% 1,1-dichloroethylbenzene by G.C. analysis (89.3% yield).

EXAMPLE 6.

Use of t-butyl hypochlorite as solvent.

Ethylbenzene (4.0 mole, 424.68 g, 492 mL) is charged to a brine jacketed reaction flask equipped with a subsurface N$_2$ sparge, light well, thermometer and condenser. The t-butyl hypochlorite (14.0 mole, 1520 g, 1670 mL) is added to the reactor and the mixture is chilled to −5° C. while sparging with N$_2$. The same lamp employed in Example 4 is switched on to initiate the reaction which is conveniently held at 0° C. by controlling the lamps' output with a temperature controller. Samples are taken periodically and analyzed by G.C. analysis. When the reaction is complete (3 hours) the mixture is drained from the reactor and the t-butanol and excess t-butylhypochlorite is removed on a rotary evaporator, leaving 709.0 g of a clear oil which is 93.2% 1,1-dichloroethylbenzene by G.C. (93% yield).

EXAMPLE 7.

Preparation of 4(1,1-dichloroethyl)-biphenyl.

A quantity of 4-ethylbiphenyl (0.41 mole, 75 g) is charged to the reactor described in Example 6 in CCl$_4$ (3.10 moles, 478.2 g, 300 mL) followed by t-butylhypochlorite (1.20 moles, 134.0 g, 147 mL). The reaction is carried out as in Example 6 and the usual work-up, using the rotary evaporator, gives 98.7 g (95.8% yield) of white crystals of 4-(1,1'-dichloroethyl)biphenyl.

EXAMPLE 8.

Preparation of bis-1,4(1,1-dichloroethyl)-benzene.

The 1,4-diethylbenzene (2.0 mole, 268.44 g, 310 mL) is charged to the reactor followed by t-butylhypochlorite (12.0 moles, 1302.84 g, 1500 mL). The reaction is carried out as in Example 6 and after the usual work-up (as in the preceding examples) there is obtained 542.34 g (99.6%) of glistening white crystals of bis-1,4-(1,1-dichloroethyl)benzene.

EXAMPLE 9.

Preparation of 4-(1,1-dichloroethyl)-phenylacetate.

Quantities of 4-ethylphenylacetate (4.0 mol, 656.8 g) and t-butylhypochlorite (12.0 mole, 1302.8 g, 1431 mL) are charged to the reactor and chilled to −5° C. The reaction is carried out as in Example 4. After the usual work-up there is obtained 857.79 g (92%) of a pale yellow oil, the 4-(1,1-dichloroethyl)phenylacetate.

EXAMPLE 10.

Preparation of 1,3,5-tris(1-chloro-1methylethyl)benzene.

A 500-mL flask equipped with stirring means and a nitrogen sparge is charged with triisopropylbenzene (TIPB, 20 g, 98 mmole) and stock t-BuOCl (2.2 moles in CCl$_4$) solution (270 mL, 590 mmole) and chilled in an ice-water bath. With stirring and nitrogen sparge, the mixture is irradiated with a 250-watt sunlamp. The temperature is kept between 10° and 25° C. by shutting off the lamp as the temperature approaches 25° and turning it back on as the temperature approaches 10° C. The reaction is continued until the solution is colorless (2 hrs). CCl$_4$ and by-product t-butanol are removed in vacuo to give 35.7 g of a cloudy oil. Pentane (30 mL) is added and the solution is chilled to −15°, giving 1,3,5- tris(1-chloro-1-methyl-ethyl)benzene as white crystals (15.8 g, 51 mmole, 52% yield), m.p. 64° (lit.69°).

EXAMPLE 11.

Preparation of 4,4'-bis(1-chloro-1-methylethyl)biphenyl.

A one-liter flask, equipped with stirring and nitrogen-sparging means, is charged with 4,4'-diisopropylbiphenyl (DIPBP, 85g, 0.36 mol) and a solution of t-BuOCl (500 mL, 1.1 mols), from the same stock solution employed in Example 10 above, and the mixture is chilled in an ice-water bath. While stirring and sparging with nitrogen, the contents are irradiated with the same type lamp used in Example 10. The temperature is maintained between 10° and 25° C. by shutting off the power when the temperature of the reaction reaches 10° C. The reaction is continued until the solution becomes colorless (ca. 2 hrs), indicating that all the t-BuOCl has been consumed. The solvent $CCl_4$ and by-product t-butyl alcohol are removed under vacuum to give 111.5g of 4,4'-bis(1-chloro-1-methylethyl)biphenyl (DIPBP-$Cl_2$). The DIPBP-$Cl_2$ is crystallized from hexane to give white crystals, m.p. 96°-98° C. This is a new compound not disclosed in the literature.

EXAMPLE 12.

Preparation of 4,4'-bis[1-(4-hydroxy-phenyl)-1-methylethyl]-biphenyl.

A one-liter flask, equipped with stirring means and a gas take-off tube connected to a water bubbler, is charged with DIPBP-$Cl_2$ (110 g, 0.36 mol) and phenol (340 g, 3.6 mols). The mixture is heated to 115° C. while stirring, using the water bubbler to maintain a slight positive pressure of HCl (a by-product of the reaction) in the flask. After 1.5 hrs, the mixture is cooled and excess phenol and HCl are removed under vacuum. The product is purified to remove residual phenol by dissolving in a minimum of boiling methanol (ca. 100 mL), adding 500 mL water and boiling with vigorous stirring for about 2 hrs. While continuing the stirring, the mixture is allowed to cool to room temperature and filtered. The solid product is dried under vacuum. The resulting tan powder is dissolved in boiling $CHCl_3$ and crystallized therefrom, giving 101.7 g of light beige crystals of 4,4'-bis[1-(4-hydroxyphenyl)-1-methylethyl]-biphenyl (BP-DIPBP), m.p. 195°-6° C. The yield is 67% of theoretical. This is a new bisphenol not previously known to the art.

The method of making aromatic polyesters from bisphenols is well known and conditions for the reaction include: (1) temperatures within the liquid ranges, e.g. from about −70° to about 300° C., preferably from about 0° to about 50° C.; (2) solvents for the reaction, such as aliphatic and aromatic hydrocarbons and their halogenated derivatives, e.g. xylene, toluene, sulfolane, dichloroethane, chloroform, methyl chloroform, chlorobenzenes and the like: (3) reactants preferably employed in tne solvent at concentrations of from about one to about 50 percent by weight based on the total reaction mixture: and (4) ratios of bisphenol to terephthalic and/or isophthalic acid or their acid chlorides of from about 0.9 to about 1.1 moles of bisphenol per mole of acid or acid chloride.

The following example illustrates the use of the bisphenol of Example 12 in making a polyester:

EXAMPLE 13.

Preparation of an aromatic polyester from BP-DIPBP.

A 1-qt blender is charged with BP-DIPBP (21.1 g, 0.0500 mole); NaOH (4.00 g, 0.100 mole); water (330 mL); and benzyltriethylammonium chloride (BTEAC, 1.5 g, 0.0065 mole) The mixture is stirred at low speed at room temperature for 10 min. A solution of isophthaloyl chloride (IPC) and terephthaloyl chloride (TPC) (5.08 g each, 0.0250 mole each) in $CHCl_3$ (150 mL) is added quickly and the mixture is blended at high speed for 10 min. The phases are separated in a separatory funnel: and the organic (heavier) phase is poured into rapidly stirring acetone (300 mL). The resulting polymer precipitate is washed with water (300 mL) and then acetone (300 mL) and then dried in a vacuum oven (100° C.) overnight. The resulting pale yellow powder has a glass transition temperature (Tg) of 237° C. and a weight-averaged molecular weight of 39,400 (relative to polystyrene standards).

A polyarylate, made under the same conditions for comparison by reacting the same ratios of phthaloyl chlorides with Bisphenol A, gives a white powder which has a Tg of 212° C. and a weight-averaged molecular weight of 31.900 (relative to polystyrene standards).

We claim:

1. A process for producing an aliphatic substituted aromatic compound having a least two alpha-halogen substituents which comprises contacting a reactive hypohalite compound with an aromatic compound, having at least one aliphatic substituent, and which contains at least two alpha-hydrogens, and in which each aliphatic substituent contains at least one beta-hydrogen in the presence of a free radical generating medium.

2. The process of claim 1 wherein the hypohalite compound is an alkyl hypohalite compound.

3. The process of claim 2 wherein the alkyl hypohalite compound is a tertiary alkyl hypohalite.

4. The process of claim 3 wherein the tertiary alkyl hypohalite is a tertiary alkyl hypochlorite.

5. The process of claim 4 wherein the tertiary alkyl hypochlorite is tertiary butyl hypochlorite.

6. The process of claim 4 wherein the tertiary alkyl hypochlorite is tertiary amyl hypochlorite.

7. The process of claim 1 wherein the hypohalite compound is an alkali or an alkaline earthmetal hypohalite.

8. The process of claim 1 wherein the hypohalite compound is a hypohalous acid.

9. The process of claim 8 wherein the hypohalous acid is hypochlorous acid.

10. The process of claim 2 wherein the free radical-generating medium is light.

11. The process of claim 10 wherein the light is in the visible spectrum.

12. The process of claim 10 wherein the light is in the ultra-violet spectrum.

13. The process of claim 2 wherein the free radical-generating medium is a compound which produces free-radicals thermally.

14. The process of claim 13 wherein the free-radical producing compound is an organic peroxide, an organic hydroperoxide or a diacylperoxide.

15. The process of claim 14 wherein the organic peroxide is t-butyl peroxide, benzoyl peroxide or isobutyroyl peroxide.

16. The process of claim 14 wherein the organic hydroperoxide is t-butyl hydroperoxide, chloro-t-butyl hydroperoxide, cumene hydroperoxide or cyclohexane hydroperoxide.

17. The process of claim 14 wherein light is also employed.

18. The process of claim 17 wherein the light is in the visible spectrum.

19. The process of claim 17 wherein the light is in the ultra-violet spectrum.

20. The process of claim 1 wherein the reaction is conducted under anhydrous conditions.

21. The process of claim 20 wherein the reaction is controlled at a temperature of from about 0° to about 25° C.

22. The process of claim 2 wherein the aromatic compound is an alkylbenzene.

23. The process of claim 22 wherein the alkylbenzene is ethylbenzene.

24. The process of claim 22 wherein the alkylbenzene is diethylbenzene.

25. The process of claim 21 wherein the alkylbenzene is triisopropylbenzene.

26. The process of claim 2 wherein the aromatic compound is an alkylbiphenyl.

27. The process of claim 26 wherein the alkylbiphenyl is ethylbiphenyl.

28. The process of claim 26 wherein the alkylbiphenyl is diisopropylbiphenyl.

29. The process of claim 2 wherein the aromatic compound is an alkylphenylacetate.

30. The process of claim 29 wherein the alkylphenylacetate is ethylphenylacetate.

* * * * *